United States Patent [19]

Niimura et al.

[11] Patent Number: 5,480,878
[45] Date of Patent: Jan. 2, 1996

[54] METHOD FOR TREATING PROSTATIC HYPERTROPHY WITH ESTRADIOL DERIVATIVES

[75] Inventors: Koichi Niimura, Warabi; Takako Kawabe, Hasuda; Tsutomu Wada, Fuchu; Tsuyoshi Saitoh, Toride; Kenji Bannai, Tokyo, all of Japan

[73] Assignee: Kureha Kagaku Kogyo Kabushiki Kaisha, Japan

[21] Appl. No.: 408,389

[22] Filed: Mar. 22, 1995

Related U.S. Application Data

[62] Division of Ser. No. 317,644, Sep. 26, 1994.

[30] Foreign Application Priority Data

Oct. 5, 1993 [JP] Japan .................. 5-273014

[51] Int. Cl.⁶ .................................. A61K 31/565
[52] U.S. Cl. .................. 514/182; 552/613; 552/614; 552/625; 552/626; 552/627
[58] Field of Search .................. 514/182; 552/613, 552/614, 625, 626, 627

[56] References Cited

U.S. PATENT DOCUMENTS

| | | | |
|---|---|---|---|
| 4,261,910 | 4/1981 | Asano et al. | |
| 4,332,797 | 6/1982 | Asano et al. | |
| 4,738,957 | 4/1988 | Laurent et al. | 514/182 |
| 4,885,290 | 12/1989 | Asano et al. | 514/182 |
| 4,921,849 | 5/1990 | Asano et al. | 514/182 |
| 4,938,897 | 7/1990 | Asano et al. | 514/169 |
| 5,036,062 | 7/1991 | Hansen | 517/176 |
| 5,354,745 | 10/1994 | Tamura et al. | |

FOREIGN PATENT DOCUMENTS

| | | |
|---|---|---|
| 93/3993 | 3/1994 | South Africa . |
| WO90/10638 | 9/1990 | WIPO . |

OTHER PUBLICATIONS

Pharmazie 38 (1983), H. 7 pp. 445–448 Mohsen et al Steroidal Derivatives "Synthesis and in vitro Anabolic and Catabolic Properties of a New Group of Steroidal Alkylating Agents".

J. Steroid Biochem. vol. 29, No. 6, pp. 657–664, 1988 Qian et al "Synthesis and Biological Activity of 17β–Substituted Estradiol".

*Primary Examiner*—Kimberly J. Kestler
*Attorney, Agent, or Firm*—Nixon & Vanderhye

[57] ABSTRACT

Disclosed is a method for treating prostatic hypertrophy with an estradiol derivative-alkylating agent conjugate of the formula (1'):

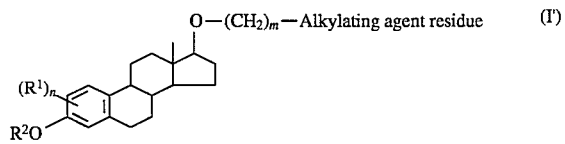

wherein $R^1$ is $C_{1-4}$ alkyl or $C_{1-4}$ alkoxy; $R^2$ is acyl or benzyl; m is an integer of 1 to 3; and n is an integer of 0 to 3. Also disclosed is the treatment of prostatic hypertrophy with an estradiol derivative of the formula (II):

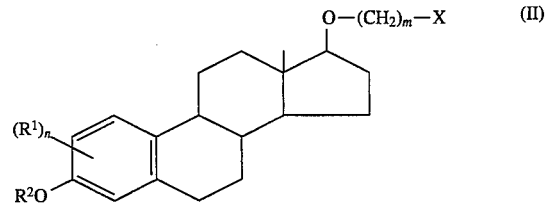

wherein $R^1$ is $C_{1-4}$ alkyl or $C_{1-4}$ alkoxy; $R^2$ is acyl or benzyl; m is an integer of 1 to 3; and n is an integer of 0 to 3; and X is hydroxy or halogen.

1 Claim, No Drawings

METHOD FOR TREATING PROSTATIC HYPERTROPHY WITH ESTRADIOL DERIVATIVES

This is a divisional of application Ser. No. 08/317,644, filed Sep. 26, 1994.

BACKGROUND OF THE INVENTION

The present invention relates to a novel estradiol derivative-alkylating agent conjugate with reduced hormonal activity, a process for preparing the conjugate, compounds useful for the preparation of the conjugate, and a growth inhibiting composition containing the conjugate or estradiol derivative.

Among the conventional alkylating agents, although having a strong antitumor activity, there are many agents which fail to display their full medicinal effects. The primary reason is their limited dosage due to their undesirable side effects in medicinal use. A solution to this problem is to combine the alkylating agent with a carrier having a specific affinity for the site of tumor to form an alkylating agent-carrier conjugate. It is intended to let the alkylating agent accumulate specifically at the site of tumor so that the agent will exhibit its antitumor activity effectively while suppressing the occurrence of the undesirable side effects.

Based on this conception, a proposal has been made on preparation of an estradiol-chlorambucil conjugate using estradiol as carrier and an antitumor agent containing the conjugate as principal constituent (Japanese Patent Publication (KOKOKU) No. 58-10397 (1983)). This antitumor agent specifically accumulates at the site of tumor and exhibits a strong antitumor activity. Further, it gives almost no significant influence to the normal cells.

However, an antitumor agent is usually required to be administered over a long period of time, so that even a slight side effect which is quite insignificant in short-term administration may give rise to a serious problem in long-time administration of the such agent. Especially, accumulation of the slight side effect may be remarkable as the physical strength of the cancer patient is usually weakened.

In the case of the estradiol-chlorambucil conjugate, in long-time administration thereof, there is observed in some cases development of the same symptoms as seen in administration of estrogen.

The studies by the present inventors have disclosed that development of such symptoms is due to the action of estrogen which is released in small quantities from the estradiol-chlorambucil conjugate in the patient's body. It is thus considered that in long-time administration of this conjugate, estrogen released in small quantities therefrom is accumulated in some cases to such an extent as to induce its side effects.

Further, the present inventors have found that when a specific substitutent, for example methyl group, is introduced into the estradiol ring, the estrogen action is remarkably diminished without impairing the selective physiological activity (growth-inhibiting action) which is inherently possessed by the estradiol-alkylating agent. It was also found that estradiol derivatives usable for the preparation of the conjugate are very low in estrogen action although they have a growth inhibiting activity. The present invention has been attained on the basis of these findings.

SUMMARY OF THE INVENTION

An object of the present invention is to provide a novel estradiol-alkylating agent conjugate which, while maintaining its original selective physiological activity, is reduced in estrogen action and of very high utility.

Another object of the present invention is to provide a process for preparing the conjugate, and estradiol derivatives useful for the preparation of the conjugate.

Still another object of the present invention is to provide a growth inhibiting agent containing the conjugate or the estradiol derivative, which agent is reduced in estrogen action.

In a first aspect of the present invention, there is provided an estradiol derivative-alkylating agent conjugate of the formula (I'):

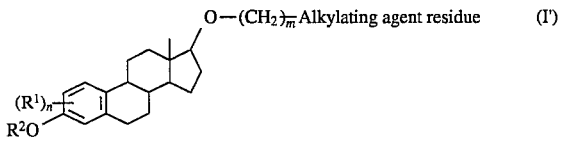

wherein $R^1$ is $C_{1-4}$ alkyl or $C_{1-4}$ alkoxy; $R^2$ is acyl or benzyl; m is an integer of 1 to 3; and n is an integer of 0 to 3.

In a second aspect of the present invention, there is provided a process for preparing the preferred conjugate, which comprises reacting an estradiol derivative of the formula (II):

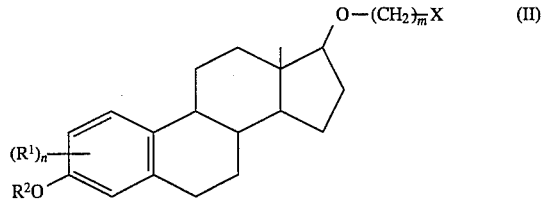

wherein $R^1$ is $C_{1-4}$ alkyl or $C_{1-4}$ alkoxy; $R^2$ is acyl or benzyl; m is an integer of 1 to 3; n is an integer of 0 to 3; and X is hydroxy or halogen; with a compound of the formula (III):

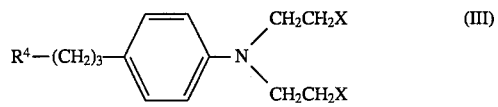

wherein $R^4$ is carboxy, hydroxy or a salt thereof, halogen, ester group, acid chloride group, acid anhydride group or methyl halide group; and X is halogen or hydroxy.

In a third aspect of the present invention, there is provided an estradiol derivative of the formula (II):

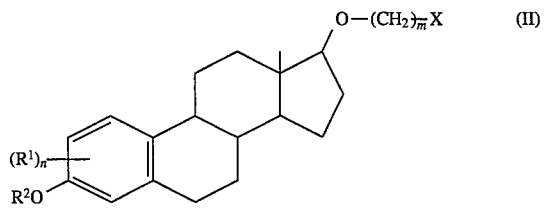

wherein $R^1$ is $C_{1-4}$ alkyl or $C_{1-4}$ alkoxy; $R^2$ is acyl or benzyl; m is an integer of 1 to 3; n is an integer of 0 to 3; and X is hydroxy or halogen.

In a fourth aspect of the present invention, there is provided a growth inhibiting composition containing an effective amount of the estradiol derivative-alkylating agent conjugate as defined in the first aspect, and a diluent.

3

In a fifth aspect of the present invention, there is provided a growth inhibiting composition containing an effective amount of an estradiol derivative of the formula (II):

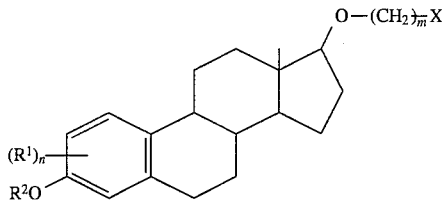
(II)

wherein $R^1$ is $C_{1-4}$ alkyl or $C_{1-4}$ alkoxy; $R^2$ is acyl or benzyl; m is an integer of 1 to 3; n is an integer of 0 to 3; and X is hydroxy or halogen, and a diluent.

DETAILED DESCRIPTION OF THE INVENTION

The conjugate of the present invention has the structure represented by the formula (I). In the formula, $R^1$ is preferably $C_{1-4}$ alkyl or $C_{1-4}$ alkoxy, more preferably methyl, and exists at the 1- or 4-position or at both of these positions. Preferably, $R^2$ is benzoyl or benzyl. Preferably, m is 2 and n is an integer of 0 to 2. More preferably, n is 1 and $R^1$ is methyl at the 1-position.

At the 3-position of the estradiol derivative moiety, hydrogen of the hydroxy is substituted with acyl or benzyl. Acyl may be $C_{1-25}$ acyl, for instance, benzoyl, acetyl, palmitoyl, stearoyl, linoleoyl or the like. Of these groups, benzoyl is preferred. The configuration at the 17-position of the estradiol derivative moiety may be β, α, or a mixture thereof, but β is preferred.

The alkylating agents usable in the present invention include chlorambucil, nitrogen mustard, melphalan and derivatives thereof including derivatives which have other halogen instead of chlorine. Preferably, the alkylating agent is chlorambucil and a derivative thereof which has other halogen instead of chlorine. The alkylating agent is bound to an estradiol derivative at a site where the antitumor activity is not impaired by the binding. Binding between alkylating agent and estradiol-derivative may be effected through the medium of an appropriate spacer.

The preferred conjugate is represented by the formula (I):

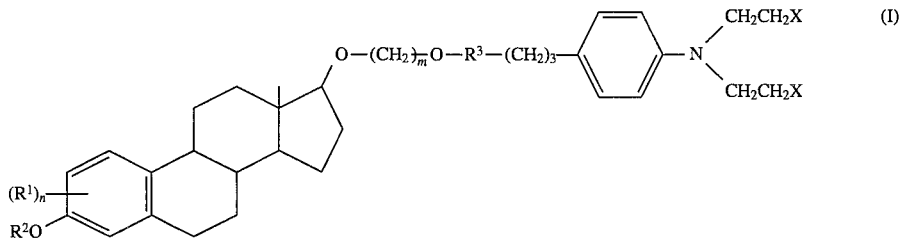

wherein $R^1$ $R^2$ m and n are as defined above, $R^3$ is carbonyl or methylene, and X is hydroxy or halogen.

Halogen is usually chlorine, bromine or iodine.

The conjugate of the present invention may be prepared, for instance, according to the following process.

First, a synthesis example of an estradiol derivative of the formula (II) is shown in Scheme 1.

Scheme 1

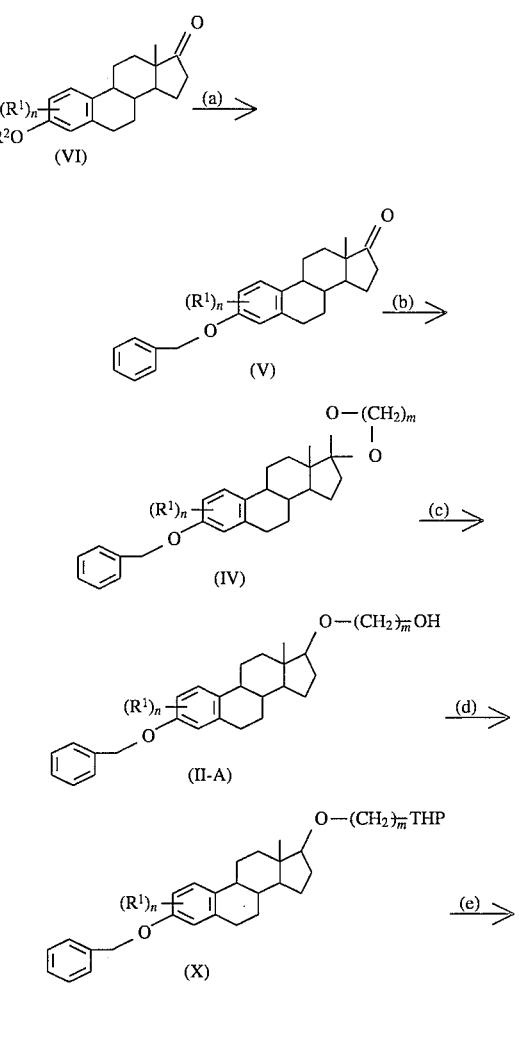

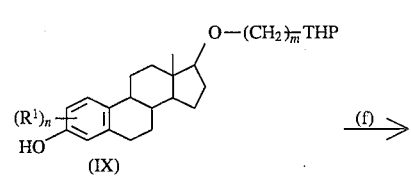

[Structure VIII shown: steroid skeleton with O-(CH₂)$_m$-THP at top, (R¹)$_n$ substituent, Acyl-O group]

$$\xrightarrow{(g)}$$

[Structure II-B shown: steroid skeleton with O-(CH₂)$_m$-OH at top, (R¹)$_n$ substituent, Acyl-O group]

The scheme is briefly described below, referring to each of the steps (a) to (g).

Step (a)

A compound of the formula (VI) (which can be prepared according to D. J. Crispin: J. Chem. Soc. (c), 10, 1970, etc.) is reacted with benzyl halide in the presence of sodium hydride at room temperature to form a compound of the formula (V).

Step (b)

The compound of the formula (V) is reacted with a $C_{1-3}$ straight-chain alkylene glycol in the presence of p-toluenesulfonic acid at 80° to 140° C. to form a compound of the formula (IV).

Step (c)

The compound of the formula (IV) is treated with lithium aluminum hydride in the presence of aluminum chloride at 30° to 70° C. to form a compound of the formula (II-A).

Step (d)

The compound of the formula (II-A) is reacted with tetrahydropyran (THP) at 4° to 60° C. to form a compound of the formula (X).

Step (e)

The compound of the formula (X) is debenzylated by treating it with Pd/C in $H_2$ gas at 0° to 30° C. to obtain a compound of the formula (IX).

Step (f)

The compound of the formula (IX) is reacted with an acyl halide at 10° to 30° C. to form a compound of the formula (VIII).

Step (g)

The compound of the formula (VIII) is detetrahydropyranated to give a compound of the formula (II-B).

The compound of the formula (II) may be converted to a salt or halide thereof. A halide can be obtained by treating a compound of the formula (II) wherein X is OH, with p-toluenesulfonyl chloride and sodium halide or the like. A salt can be obtained by the conventional method.

In the estradiol derivatives of the formula (II), preferably $R^1$ is $C_{1-2}$ alkyl or $C_{1-2}$ alkoxy, $R^2$ is benzoyl or benzyl, m is 2 and n is an integer of 0 to 2. Most preferably, $R^1$ is methyl and exists at the 1- and/or 4-position, especially at the 1-position.

Then, the estradiol derivative is combined with the desired alkylating agent.

In case that the alkylating agent is chlorambucil or a derivative thereof, the estradiol derivative of the formula (II) is reacted with a compound of the formula (III):

[Structure III: $R^4$—(CH₂)$_3$—phenyl—N(CH₂CH₂X)(CH₂CH₂X)]     (III)

where $R^4$ is carboxy, hydroxy or a salt thereof, halogen, ester group, acid chloride group, acid anhydride group or methyl halide group; and X is halogen or hydroxy, to form a conjugate of the formula (I). The reaction can be carried out in an organic solvent such as dichloromethane, dioxane, dimethyl sulfoxide, dimethylformamide, pyridine, benzene, acetone, toluene, carbon tetrachloride, chloroform, tetrahydrofuran or the like. An alkali solution, sodium hydride, thionyl chloride and the like may be added as desired. The reaction may be performed at 30° to 150° C., preferably −10° to 100° C., for 3 minutes to 48 hours, preferably 5 minutes to 24 hours. The reaction product is purified by a usual method to give the conjugate of the present invention.

The conjugate of the formula (I) in which the 3-position of the estradiol is benzyloxy is debenzylated by treating it with Pd/C in the presence of $H_2$ and then further reacted with an acid chloride or acid anhydride corresponding to the objective acyl to provide the conjugate of the present invention in which the 3-position of the estradiol is acyloxy.

Known methods such as extraction, chromatography, crystallization, reprecipitation, etc., can be applied for purification of the reaction product.

The toxicity and pharmacological actions, as determined by the following methods, of the conjugate and the estradiol derivative of the present invention are described below.

(1) Toxicity

The conjugate and the estradiol derivative were each administered intraperitoneally to the ICR mice at a dose of 100 mg/kg and the test mice were placed under observation for one week. As a result, no death was observed.

(2) Estrogen action (uterine weight tests)

The estrogen action of the conjugate and the estradiol derivative were each examined according to the uterine weight tests. The estrogen action was found diminished.

(3) Growth inhibiting effect ($IC_{50}$) in testosterone-added system using breast cancer cells (SC-115)

Uptake of tritium-labeled thymidine was examined in a serum free culture system using testosterone-dependent SC-115 cells. Strong inhibitory effects of the conjugate and the estradiol derivatives were shown. (4) Growth inhibiting effect ($IC_{50}$) in bFGF-added system using prostatic cancer cells (DC-145)

Uptake of tritium-labeled thymidine was examined in a serum free culture system using bFGF-dependent DU-145 cells. Strong inhibitory effects of the conjugate and the estradiol derivative were shown.

The conjugate of the formula (I) and the estradiol derivatives of the formula (II) are excessively weakened in estrogen action and low in toxicity and also have a growth inhibiting action, so that they are useful as a growth inhibiting agent. The substances also show a growth inhibiting action against tumor cells, so that they can be applied as an antitumor agent. They are effective against various types of cancers such as breast cancer, ovarian cancer, uterine cancer, prostatic cancer, stomach cancer, rectal cancer, colonic cancer, renal cancer, cancer of hematopoietic organ, liver cancer, cancer of urinary organ, and other solid cancers. The conjugate and the estradiol derivative also have an inhibiting action against prostatic hypertrophy and are therefore useful as an anti-prostatic hypertrophy agent.

For use of the conjugate and the estradiol derivative as a growth inhibiting agent, it can be prepared into various forms suited for the ways of administration in combination with a diluent (carrier) according to the known methods. In case of preparation of a pharmaceutical composition, a pharmaceutically acceptable diluent is used. The forms of composition include capsule, syrup, oral preparations such as pills and tablets, injections, external preparations, suppository, etc. The external preparations include solid agents containing a percutaneous penetration auxiliary such as lauric acid diethanol amide in an ordinary base such as white vaseline.

In the composition, the conjugate and the estradiol derivative each may be contained in an amount of preferably 0.01 to 75% by weight, more preferably 0.05 to 25% by weight. The conjugate and the estradiol derivative can be administered through various routes such as peroral, percutaneous, intramuscular, intravenous, intraarterial, intrarectal, etc. The dosage is variable depending on the way of administration and the degree of treatment, but generally it is 0.1 to 50 mg/kg per day in the case of peroral administration and 0.01 to 20 mg/kg per day in the case of parenteral administration, both for adults.

The estradiol derivative moiety in the conjugate of the present invention has an ether linkage at the 17-position in addition to a substitutent at the 3-position of the A ring. This structure is considered to lend itself to excessive diminution of the estrogen action while allowing maintenance of the growth inhibiting action which is inherently possessed by the estradiol-alkylating agent conjugate, thus remarkably enhancing the utility of the conjugate as a growth inhibiting agent.

EXAMPLES

The following examples further illustrate the present invention. These examples are merely intended to be illustrative and not to be taken as limiting the scope of the invention. "%" is by weight, unless otherwise noted. The properties of the compounds were determined by using the following material or apparatus.
(1) Thin layer chromatography (silica gel): Merck's Kieselgel 60 $F_{254}$
(2) Elemental analysis: Yanagimoto C. H. N. Coder MT-3 (Yanagimoto Ltd.)
(3) Mass spectrometry: Mass Spectrometer JMS-DX 303 (Nippon Denshi KK)
(4) NMR ($CDCl_3$): JNM-GSX-500 (Nippon Denshi KK)
(5) Infrared absorption spectrometry: Infrared Spectrophotometer A-202 (Nippon Bunko KK)

Example 1

Synthesis of 3-benzyloxy-1,3,5 (10)-estratriene-17-one (V-1)

3-Hydroxy-1,3,5 (10)-estratriene-17-one (VI-1) (2.70 g), distilled tetrahydrofuran (THF) (20 ml) and dimethylformamide (DMF) (4 ml) were mixed and dissolved in an eggplant type flask (300 ml). To this solution were added sodium hydride (0.24 g) and benzyl bromide (1.88 g), and the mixture was stirred overnight at room temperature. Distilled water was added to the reaction solution, and the solution was extracted with ethyl acetate (100 ml), followed by additional extraction with ethyl acetate (50 ml). The organic layers were washed with distilled water and a saturated saline solution. The washings were dried over anhydrous sodium sulfate and concentrated under reduced pressure to give the objective compound (V-1) (3.48 g) as crystals.

Yield: 96.5%

Elemental analysis, calcd. for $C_{25}H_{28}O_2$: Found: C, 82.65; H, 7.82. Calcd.: C, 83.29; H, 7.83.

Melting point: 129.2°–130.8° C.

$^1$H-NMR ($CDCl_3$, δ ppm): 0.91 (s, 3H), 1.39-1.66 (m, 8H), 1.94–2.08 (m, 3H), 2.12–2.17 (m, 1H), 2.25 (m, 1H), 2.37 (m, 1H), 2.49 (m, 1H), 2.89 (m, 2H), 5.04 (s, 2H), 6.73 (s, 1H), 6.79 (dd, 1H), 7.20 (d, 1H), 7.31 (t, 1H), 7.38 (t, 2H), 7.42 (d, 2H).

IR (KBr, νmax): 3460 m, 3080 m, 3050 m, 2940 s, 2980 s, 1738 s, 1605 s, 1580 m, 1510 s.

Rf: 0.46 (hexane/ethyl acetate=2:1)

Example 2

Synthesis of 3-benzyloxy-1,3, 5 (10)-estratriene-17-cycloethylene ketal (IV-1)

Benzene was added to 3-benzyloxy-1,3,5 (10)-estratriene-17-one (V-1) (0.11 g), ethylene glycol (0.23 g) and p-toluenesulfonic acid (0.6 rag). This mixture was azeotropically boiled at 120° C. by a Dean-Stark apparatus and stirred overnight. An excess amount of triethylamine was added to the reaction solution to neutralize, and the mixed solution was concentrated under reduced pressure and extracted with ethyl acetate (50 ml). The organic layer was washed with distilled water, dried over anhydrous sodium sulfate and concentrated under reduced pressure to produce the crystals (0.14 g). These crystals were purified by silica gel chromatography (hexane/ethyl acetate =4:1) to give the objective compound (IV-I) (0.11 g) as white crystals.

Yield: 94.0%.

Elemental analysis, calcd. for $C_{27}H_{32}O_3$: Found: C, 79.81; H, 7.96. Calcd.: C, 80.16; H, 7.97.

Melting point: 124.5°–125.5° C.

$^1$H-NMR ($CDCl_3$, δ ppm): 0.88 (s, 3H), 1.32–1.57 (m, 6H), 1.64 (m, 1H), 1.74-1.91 (m, 4H), 2.03 (m, 1H), 2.24 (m, 1H), 2.31 (m, 1H), 2.84 (m, 2H), 5.03 (s, 2H), 3.87–3.98 (m, 4H), 6.71 (s, 1H), 6.77 (dd, 1H), 7.20 (d, 1H), 7.30 (m, 1H), 7.37 (t, 2H), 7.42 (d, 2H).

IR (KBr, ν max): 3460 m, 3100 m, 3070 m, 3020 s, 2950 s, 2910 s, 2850 s, 1610 s, 1590 m.

Rf: 0.56 (hexane/ethyl acetate =2:1)

Example 3

Synthesis of 2- [3-benzyloxy-1,3,5 (10)-estratriene-17β-oxy]ethanol (II-1)

Aluminum chloride (14.9 mmol) and anhydrous ether (4 ml) were placed into an eggplant type flask (100 ml) at 0° C., and the solution was stirred for 30 minutes. To this solution was added a suspension of lithium aluminum hydride (3.6 mmol) and anhydrous ether (4 ml), and the mixture was stirred for additional 30 minutes. To this solution was added an anhydrous ether (20 m!) solution of 3-benzyloxy-1,3, 5(10)-estratriene-17-cycloethylene ketal (IV-1) (3.6 mmol), and the mixed solution was refluxed under heating at about 50° C. for 3 hours, followed by addition of distilled water at 0° C. This solution was transferred into an eggplant type flask (500 ml) and the solute was extracted with diethyl ether (200 ml). The organic layer was dried over anhydrous sodium sulfate and concentrated under reduced pressure to produce the crystals (1.34 g). These crystals were washed with hexane to give the objective compound (II-1) (1.20 g) as white crystals.

Yield: 81.0%.

Elemental analysis, calcd. for $C_{27}H_{32}O_3$: Found: C, 79.43; H, 8.43. Calcd.: C, 79.77; H, 8.43.

Melting point: 82.8°–84.3° C.

$^1$H-NMR (CDCl$_3$, δ ppm): 0.80 (s, 3H), 1.20 (m, 1H), 1.30–1.57 (m, 7H), 1.68 (m, 1H), 1.68 (m, 1H), 2.01–2.07 (m, 5H), 2.23 (m, 1H), 2.83 (m, 2H), 3.43 (t, 1H), 3.56 (m, 1H), 3.61 (m, 1H), 3.70 (m, 2H), 5.02 (s, 2H), 6.70 (s, 1H), 6.77 (dd, 1H), 7.19 (d, 1H), 7.30 (m, 1H), 7.37 (t, 2H), 7.42 (d, 2H).

IR (KBr, ν max): 3460 s, 3100 m, 3260 m, 2950 s, 2900 s, 1610 s, 1590 m, 1515 s.

Rf: 0.22 (hexane/ethyl acetate =2:1)

Example 4

Synthesis of 2- [3-benzoyloxy-1,3,5(10)-estratriene-1-methyl-17β-oxy]ethanol (II-3)

2- [3-benzyloxy-1,3,5(10) -estratriene-1-methyl-17βoxy-]ethanol (II-2) (m.p.: 103.5°–104.5° C.) (2.31 g) produced according to the process of Example 3 and dichloromethane (15 ml) were placed and dissolved in an eggplant type flask (100 ml). To this solution were added dihydropyran (924 mg) and pyridinium p-toluenesulfonate (PPTS) (138 mg), and the mixture was stirred overnight at room temperature. The reaction solution was distilled, and the residue was dissolved in ethyl acetate (50 ml), washed twice with water (15 ml) and further washed with a saturated saline solution (15 ml). The washings were dried over Na$_2$SO$_4$, filtered and distilled to form an oily substance (3.19 g). This substance was purified by silica gel chromatography (hexane/ethyl acetate =5:1) to give a purified product (2.42 g). The progress of the reaction was confirmed by TLC check. The purified product was dissolved in dioxane (238 ml) and 10% Pd/C was added to the solution. This solution was treated with H$_2$gas at room temperature for 5 hours to obtain a debenzylated compound (1.77 g). This compound was dissolved in dry dichloromethane (30 ml), followed by addition of pyridine (8.5 ml) and benzoyl chloride (596.0 ml), and the mixed solution was stirred overnight at room temperature. The stirred solution was distilled and the residue was dissolved in ethyl acetate (60 ml), washed twice with water (20 ml) and further washed with a saturated saline solution (20 ml). The washings were distilled and the residue was crystallized. The crystallized product was filtered out, collected and washed with hexane (3 ml) to produce a benzoyl compound (1.53 g). This compound was dissolved in ethanol (85 ml) and PPTS (1.24 g), and the solution was stirred at 40° C. for 2 hours and distilled. The residue was dissolved in ethyl acetate (100 ml) and washed with water (30 ml) and a hydrochloric acid solution (1N, 30 ml). The organic layer was dried over Na$_2$SO$_4$, filtered and distilled. The residue was crystallized, again dissolved in ethyl acetate/hexane (1:3) (50 ml) and recrystallized. The produced crystals were filtered out, washed with hexane (20 ml) and dried in vacuo to give the objective compound (II-3) (1.07 g) as white needle crystals.

Melting point: 185°–187° C.

$^1$H-NMR (CDCl$_3$, δ ppm): 0.80 (s, 3H), 1.24 (m, 2H), 1.37 (m, 2H), 1.45 (m, 2H), 1.67 (m, 1H), 1.80 (m, 2H), 2.00 (m, 1H), 2.23 (s, 3H), 2.37 (t, 1H), 2.65 (m, 2H), 2.72 (m, 1H), 3.35 (t, 1H), 3.50 (m, 2H), 3.64 (m, 2H), 6.84 (d, 1H), 7.04 (d, 1H), 7.51 (m, 2H), 7.64 (m, 1H), 8.18 (m, 2H).

IR (KBr, ν max): 3500 br, 2950 m, 2880 m, 1735 s, 1600 w, 1580 w, 1450 m, 1380 w, 1340 w, 1320 w, 1265 s, 1220 s, 1160 m, 1100 m, 1085 s.

Mass spectrum (m/e): 434 (M$^+$), 416, 312, 268, 251, 227.

Example 5

Synthesis of 1- [3-benzyloxy-1,3,5(10) -estratriene-17β-oxy]-2-[4-[p-[bis(2-chloroethyl) amino]phenyl]butoxy]ethane (I-1)

2- [3-benzyloxy-1,3,5(10 ) -estratriene-17β-oxy]ethanol (II-1) (61 mg) and distilled DMF (0.5 ml) were placed and dissolved in an eggplant type flask (200 ml). To this solution was added sodium hydride (5 mg) at 0° C., followed by further addition of 4- [p-[bis (2-chloroethyl)amino]phenyl] iodobutane (Rf=0.64, phosphomolybdic acid reagent) (90 mg) at 0° C., and the mixture was stirred for 3 hours. Distilled water was added to the reaction solution, and the solution was extracted twice with ethyl acetate (50 ml). The organic layers were washed with a saturated saline solution (50 ml), and the washings were dried over anhydrous sodium sulfate and concentrated under reduced pressure to give an oily substance (0.19 g). This oily substance was purified by silica gel chromatography (hexane/ethyl acetate =6:1) to give the objective compound (I-1) (56.1 mg) as an oily substance.

Yield: 55.1%.

$^1$H-NMR (CDCl$_3$, δ ppm): 0.79 (s, 3H), 1.19 (m, 1H), 1.29–1.58 (m, 10H), 1.63 (m, 4H), 1.86 (m, 1H), 2.03 (m, 2H), 2.15 (m, 1H), 2.25 (m, 1H), 2.54 (t, 2H), 2.83 (m, 2H), 3.43 (t, 1H), 3.50 (t, 2H), 3.55 (t, 2H), 3.59 (s, 5H), 3.66 (m, 5H), 5.03 (s, 2H), 6.61 (d, 2H), 6.70 (d, 1H), 6.77 (dd, 1H), 7.06 (d, 2H), 7.18 (d, 1H), 7.31 (t, 1H), 7.37 (t, 2H), 7.42 (d, 2H).

IR (KBr, ν max): 2950 s, 2870 s, 1638 s, 1575 m, 1525 s, 1510 s, 1455 m.

Rf: 0.58 (hexane/ethyl acetate =2:1).

Example 6

Synthesis of 1-[3-benzoyloxy-1,3,5(10)-estratriene-17β-oxy]-2-[4-[p-[bis(2-chloroethyl)amino]phenyl]butoxy]ethane (I-2)

10% palladium on carbon (83.1 mg) was added at 0° C. into an eggplant type flask (100 ml), followed by piecemeal addition of 1,4-dioxane (3 ml). To this solution was added a 1,4-dioxane (5 ml) solution of 1-[3-benzyloxy-1,3,5(10) -estratriene-17β-oxy]-2-[4-[p-[bis(2-chloroethyl)amino] phenyl]butoxy]ethane (I-1) (0.11 g) piecemeal at 0° C. The mixture was heated to room temperature and stirred under hydrogen gas for 2 hours. This reaction mixture was filtered through filter paper while washing with 1,4-dioxane, and the filtrate was concentrated under reduced pressure to produce an oily substance (92.7 mg). This oily substance was dissolved in dichloromethane (0.5 ml), followed by addition of pyridine (0.3 ml) and benzoyl chloride (0.02 ml) at 0° C., and stirred overnight at room temperature. The reaction solution was extracted with ethyl acetate (50 ml) and the extract was washed with a saturated saline solution. The washings were dried over anhydrous sodium sulfate and concentrated under reduced pressure to produce an oily substance (116.7 mg). It was purified by silica gel chromatography (hexane/ethyl acetate =4:1) to give the objective compound (I-2) (74.1 mg) as white crystals.

Melting point: 96.8°–98.7° C.

Mass spectrum (m/e): 705 (M$^+$)

Rf: 0.54 (hexane/ethyl acetate =2:1)

In the same way, 1-[3-benzoyloxy-1,3,5(10)-estratriene-1-methyl-17β-oxy]-2-[4-[p-[bis (2-hydroxyethyl)amino]phenyl]butoxy]ethane (I-3) was synthesized.

Rf: 0.36 (n-hexane/ethyl acetate=2:1 )

Mass spectrum (m/e): 705 (M$^+$), 656, 371, 224, 105.

IR; 3095W, 2950 s, 2880 s, 1740 s, 1622 s, 1525 s, 1460 s, 1396 m, 1360 s.

There was also similarly synthesized 1-[3-benzoyloxy-1,3,5 (10)-estratriene-17β-oxy]-2-[4-[bis(2-hydroxyethyl)amino]-phenyl]butoxy]ethane (I-4) .

EXAMPLE 7

Synthesis of 1-[3-benzyloxy-1,3,5(10)-estratriene-17β-oxy]-2-[4-[p-[bis(2-chloroethyl)amino]phenyl]-butyryloxy]ethane (I-5)

2- [3-benzyloxy-1,3,5(10) -estratriene-17β-oxy]ethanol (II-1) and dichloromethane (5 ml) were placed and dissolved in an eggplant type flask (300 ml), followed by addition of pyridine (95 ml) at 0° C. To this solution, chlorambucil (0.3 g) and excess thionyl chloride were added dropwise and stirred at room temperature for about 5 minutes. Benzene was added to this reaction solution, and the solution was concentrated under reduced pressure three times. To the residue was added a small quantity of dichloromethane while washing therewith at 0° C., and the mixture was stirred overnight. The reaction mixture was poured into cold water, and the mixture was extracted twice with diethyl ether (50 ml). The organic layers were dried over anhydrous sodium sulfate and concentrated under reduced pressure to produce an oily substance (0.72 g). It was purified by silica gel chromatography (hexane/ethyl acetate =4:1) to give the objective compound (I-5) (0.49 g).

Yield: 71.1%.

$^1$H-NMR (CDCl$_3$, δ ppm): 0.78 (s, 3H), 1.18 (m, 1H), 1.29–1.58 (m, 6H), 1.67 (m, 1H), 1.87 (m, 1H), 1.92 (d, 2H), 2.18 (m, 1H), 2.25 (m, 1H), 2.35 (t, 2H), 2.5 (t, 2H), 2.84 (m, 2H), 3.42 (t, 1H), 3.60 (m, 5H), 3.67 (m, 5H), 4.21 (t, 2H), 5.03 (s, 2H), 6.64 (d, 2H), 6.71 (s, 1H), 6.77 (dd, 1H), 7.07 (d, 1H), 7.18 (d, 1H), 7.31 (t, 1H), 7.37 (t, 2H), 7.42 (d, 2H).

IR (KBr, ν max): 3460 m, 3080 m, 3050 m, 2940 s, 2980 s, 1738 s, 1605 s, 1580 m, 1510 s.

Rf: 0.54 (hexane/ethyl acetate =2:1)

Mass spectrum (m/e): 691 (M$^+$), 637.

EXAMPLE 8

Synthesis of 1-[3-benzoyloxy-1,3,5(10)-estratriene-17β-oxy]-2-[4-[p-[bis(2-chloroethyl)amino]phenyl]butyryloxy]ethane (I-6)

10% palladium on carbon (320.7 mg) was placed into an eggplant type flask (100 ml), followed by dropwise addition of 1,4-dioxane (15 ml) at 0° C. To this mixture was added a 1,4-dioxane (15 ml) solution of 1-[3-benzyloxy-1,3,5(10)-estratriene-17β-oxy]-2-[4-[p-[bis(2-chloroethyl) amino] phenyl]-butyryloxy]ethane (I-5) dropwise at 0° C. The mixture was heated to room temperature and stirred under hydrogen gas for one hour. The reaction mixture was filtered through filter paper while washing with 1,4-dioxane, and the filtrate was concentrated under reduced pressure to produce an oily substance (0.27 g). It was purified by silica gel chromatography (hexane/ethyl acetate =3:1) to obtain 1-[3-hydroxy-1,3,5(10)-estratriene-17β-oxy]-2-[4-[p-[bis(2-chloroethyl)amino]phenyl]butyryloxy]ethane (0.26 g) (Rf: 0.25, hexane/ethyl acetate =3:1) as oily substance.

To a 1,4-dioxane (1 ml) solution of this oily substance, pyridine (0.8 ml) and benzoyl chloride (0.1 ml) were added at 0° C. and stirred at room temperature for 2.5 hours. The reaction solution was extracted with ethyl acetate (50 ml) and the extract was washed with a saturated saline solution. The washings were dried over anhydrous sodium sulfate and concentrated under reduced pressure to produce an oily substance (0.36 g). This oily substance was purified by silica gel chromatography (hexane/ethyl acetate =4:1) to give the objective compound (I-6) (0.12 g) as white crystals.

Yield: 71.1%.

Elemental analysis, calcd. for C$_{41}$H$_{49}$O$_5$NCl$_2$: Found: C, 68.87; H, 6.84; N, 2.12. Calcd.: C, 69.68; H, 6.99; N, 1.98.

Melting point: 113.7°–115.0° C.

$^1$H-NMR (CDCl$_3$, δ ppm): 0.80 (s, 3H), 1.35-1.57 (m, 8H), 1.93 (m, 2H), 2.21 (m, 2H), 2.36 (t, 2H), 2.58 (t, 2H), 2.88 (m, 2H), 3.43 (t, 1H), 3.61 (m, 5H), 3.68 (m, 5H), 4.21 (t, 2H), 6.65 (d, 2H), 6.92 (s, 1H), 6.97 (d, 1H), 7.08 (d, 2H), 7.32 (d, 1H), 7.50 (t, 2H), 7.63 (t, 1H), 8.19 (d, 2H).

IR (KBr, ν max): 2990 m, 2950 m, 2900 m, 1755 s, 1735 s, 1620 m, 1610 m, 1530 m, 1515 m.

Rf: 0.48 (hexane/ethyl acetate =2:1).

Mass spectrum (m/e): 105 (Ph-CO), 128 (2CH$_2$CH$_2$Cl), 656 (MC-CH$_2$Cl), 705 (M$^+$).

EXAMPLE 9

Toxicity test

The compounds of the present invention dissolved in sesame oil (containing 3% benzyl alcohol) were each administered once intraperitoneally to 6-week-old ICR female mice (average body weight: 25 g) at a dosage of 100 mg/kg. The test mice were observed for a period of 7 days after administration of the compounds. No death was observed in any case of the compounds.

EXAMPLE 10

Estrogen action (uterine weight tests)

The test compounds and estradiol dissolved in sesame oil (containing 3% benzyl alcohol) were each administered once hypodermically to 3-week-old Wistar female rats. 24 hours later, the uterus of each test rat was removed and its weight (ratio to the body weight) was measured. From the relation between the uterus weight/body weight ratio and the dosage, the compound dosage that gives a uterus weight/body weight ratio twice that in the control group was determined. The dosages of the test compounds are shown as a ratio to the dosage of estradiol. 3-Benzoyloxy-1,3,5(10)-estratriene-17β-[4-[p-[bis(2-chloroethyl)amino]phenyl]-butyryloxy]acetate was used as a comparative compound. The results are shown in Table 1.

TABLE 1

| Test compound | Dosage that gives a uterus wt/body wt ratio twice that in control group (ratio to estradiol dosage) |
|---|---|
| II-1 | 200 |
| II-2 | >7000 |
| II-3 | >7000 |
| I-1 | >7000 |
| I-2 | >7000 |
| I-3 | >7000 |
| I-4 | 1400 |
| I-5 | >7000 |
| I-6 | >7000 |
| Comparative compound | 200 |

EXAMPLE 11

Growth inhibiting effect ($IC_{50}$) in testosterone-added system using SC-115 cells The SC-115 cells were cultured on a 96-well microplate (5,000 cells/well) for 24 hours with a culture medium (200 μl/well; Ham's F-12/MEM-E (98%), dextran-treated fetal calf serum (2%) and testosterone ($1\times10^{-8}$M)). The culture medium was replaced with fresh medium containing the test compound (Ham's F-12/MEM-E, bovine serum albumin (0.1%), testosterone ($1\times10^{-8}$M) and test compound of various concentrations). The culture medium was replaced every two days, and culture was continued for 7 days. Thymidine (1 μci/ml, tritium-labeled) was added, and 5 hours later, the culture medium was removed. The cells were washed with PBS and then washed twice with ice-cold trichloroacetic acid (10%). Then the cells were dissolved in 0.5N sodium hydroxide and neutralized with 0.5N hydrochloric acid. The radioactivity of the neutralized solution was measured by a liquid scintillation counter to determine the growth inhibiting effect ($IC_{50}$). The results are shown in Table 2.

TABLE 2

| Test compound | $IC_{50}$ (μM) |
|---|---|
| II-1 | 0.2 |
| II-2 | 0.7 |
| II-3 | 1.5 |
| I-1 | 1.2 |
| I-2 | 1.3 |
| I-3 | 0.2 |
| I-4 | 0.8 |
| I-5 | 0.5 |
| I-6 | 1.5 |
| Comparative Compound | 2.6 |

EXAMPLE 12

Growth inhibiting effect ($IC_{50}$) in bFGF-added system using DU-145 cells

The DU-145 cells were cultured on a 96-well microplate (5,000 cells/well) for 24 hours with a culture medium (200 μl/well; Ham's F-12/MEM-E (98%) and dextran-treated fetal calf serum (2%)). Then the culture medium was replaced with fresh medium containing the test compound (Ham's F-12/MEM-E, bovine serum albumin (0.1%), bovine pituitary-derived bFGF (1 ng/ml) and the test compound of various concentrations). Culture with this medium was continued for 4 days. Thymidine (1 μci/ml, tritium-labeled) was added, and 5 hours layer, the culture medium was removed. The cells were washed with PBS and then washed twice with ice-cold trichloroacetic acid (10%). Then the cells were dissolved in 0.5N sodium hydroxide and neutralized with 0.5N hydrochloric acid. The radioactivity of the neutralized solution was measured by a liquid scintillation counter to determine the growth inhibiting effect ($IC_{50}$). The results are shown in Table 3.

TABLE 3

| Test compound | $IC_{50}$ (μM) |
|---|---|
| II-1 | 2.9 |
| I-1 | 4.6 |
| I-2 | 7.8 |
| I-3 | 9.2 |
| Comparative Compound | ND* |

*Under the experimental conditions, no inhibiting action against growth of the cells was observed at the concentrations (0.1 to 10 μM) in the range of measurement.

EXAMPLE 13

| Preparation example | (by weight) |
|---|---|
| Compound of the present invention (I-1) | 30 parts |
| Mannitol | 35 parts |
| Sorbitol | 25 parts |
| Carboxymethyl cellulose | 5 parts |
| Magnesium stearate | 5 parts |
| Talc | 40 parts |

The above components were mixed well and the mixture was compressed into 10-mm diameter tablets.

What is claimed is:

1. A method for treatment of prostatic hypertrophy, which comprises administering to a patient suffering from prostatic hypertrophy, an effective amount of an estradiol derivative-alkylating agent conjugate of the formula (I'):

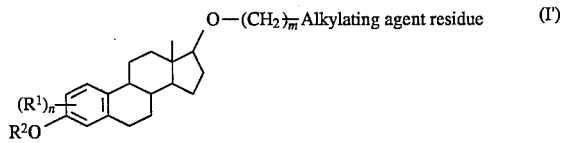

wherein $R^1$ is $C_{1-4}$ alkyl or $C_{1-4}$ alkoxy; $R^2$ is acyl or benzyl; m is an integer of 1 to 3; and n is an integer of 0 to 3, or an effective amount of an estradiol derivative of the formula (II):

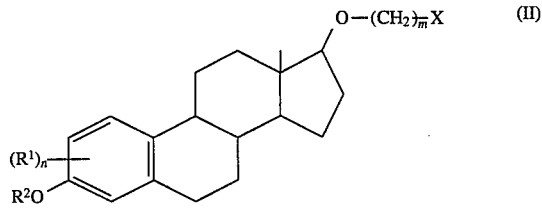

wherein $R^1$ is $C_{1-4}$ alkyl or $C_{1-4}$ alkoxy; $R^2$ is acyl or benzyl; m is an integer of 1 to. 3; n is an integer of 0 to 3; and X is hydroxy or halogen.

* * * * *

UNITED STATES PATENT AND TRADEMARK OFFICE
CERTIFICATE OF CORRECTION

PATENT NO. : 5,480,878  Page 1 of 2
DATED : January 2, 1996
INVENTOR(S) : NIIMURA et al.

It is certified that error appears in the above-identified patent and that said letters patent is hereby corrected as shown below:

Column 3, line 58, change "$R^1 R^2$ m and n" to read -- $R^1$, $R^2$, m and n --.

Column 6, line 54, insert a character return after "were shown." so that text which follows the same may be read as a title:

"(4) Growth inhibiting effect ($IC_{50}$) in bFGF-added system using postatic cancer cells (DC-145)".

Column 8, line 28 change "(0.6 rag)" to read -- (0.6 mg) --;
line 63, change "(20 m! ) to read -- (20 ml) --.

Column 9, line 29, change "17βoxy-" to read -- 17-β-oxy- --.

Column 10, line 19, change "1, 3, 5 (10 ) - estratrtiene" to read -- 1,3,5(10)-estratriene --.

Column 11, line 11, change "[bis    (2-" to read -- [bis (2- --;
line 16, change "3095W" to read -- 3095w --;
line 19, change "3,5    (10)" to read -- 3,5(10) --;
line 66, change "(2-chloroethyl)    amino] to read -- (2-chloroethyl)amino]-- .

UNITED STATES PATENT AND TRADEMARK OFFICE
CERTIFICATE OF CORRECTION

PATENT NO. : 5,480,878
DATED : January 2, 1996
INVENTOR(S) : NIIMURA et al.

It is certified that error appears in the above-indentified patent and that said Letters Patent is hereby corrected as shown below:

Column 14, line 14, change "1 to. [period] 3" to -- 1 to 3 --.

Signed and Sealed this

Twenty-second Day of October, 1996

*Attest:*

BRUCE LEHMAN

*Attesting Officer*     Commissioner of Patents and Trademarks